United States Patent [19]
Yaginuma

[11] Patent Number: 5,912,776
[45] Date of Patent: Jun. 15, 1999

[54] INTERIOR IMAGE RECEIVING APPARATUS

[75] Inventor: Yoshitaka Yaginuma, Naka-gun, Japan

[73] Assignee: Mitsubishi Nuclear Fuel Co., Tokyo, Japan

[21] Appl. No.: 08/938,451

[22] Filed: Sep. 29, 1997

[30] Foreign Application Priority Data

Oct. 24, 1996 [JP] Japan ................................. 8-282688
Jan. 30, 1997 [JP] Japan ................................. 9-017146

[51] Int. Cl.⁶ .......................... G02B 5/08; G01N 21/88
[52] U.S. Cl. ................ 359/850; 356/239.4; 356/240.1; 250/223 B
[58] Field of Search .................... 359/726, 727, 359/850, 864, 867, 868, 869; 356/240, 428, 239.4, 239.5, 239.6, 240.1; 250/223 B

[56] References Cited

U.S. PATENT DOCUMENTS

| | | | |
|---|---|---|---|
| 4,283,145 | 8/1981 | Miyazawa | 356/240 |
| 4,758,084 | 7/1988 | Tokumi et al. | 356/240 |
| 4,912,318 | 3/1990 | Kajiura et al. | 356/240 |
| 4,959,538 | 9/1990 | Swart | 356/240 |
| 5,030,823 | 7/1991 | Obdeijn | 250/223 B |
| 5,045,688 | 9/1991 | Domenico et al. | 250/223 B |
| 5,103,087 | 4/1992 | Hofliger et al. | 356/240 |
| 5,126,556 | 6/1992 | Domenico et al. | 356/240 |
| 5,699,152 | 12/1997 | Fedor et al. | 250/223 B |

FOREIGN PATENT DOCUMENTS

| | | | |
|---|---|---|---|
| 0047936 | 3/1982 | European Pat. Off. | 356/428 |
| 0 371 547 | 6/1990 | European Pat. Off. | |
| 0371546 | 6/1990 | European Pat. Off. | 356/240 |
| 0 708 325 | 4/1996 | European Pat. Off. | |
| 3035077 | 4/1982 | Germany | 356/240 |
| 0098340 | 6/1985 | Japan | 356/240 |
| WO 96/31768 | 10/1996 | WIPO . | |

*Primary Examiner*—Ricky D. Shafer
*Attorney, Agent, or Firm*—Oblon, Spivak, McClelland, Maier & Neustadt, P.C.

[57] ABSTRACT

An interior image receiving apparatus which includes an image receiver positioned facing an opening of a hollow object. Also included is a reflecting mirror positioned between the image receiver and the opening, in which the image receiver receives an image of the inner surface of the object reflected by the mirror.

19 Claims, 6 Drawing Sheets

INTERIOR IMAGE RECEIVING APPARATUS

BACKGROUND OF THE INVENTION

The present invention relates to an interior image receiving apparatus for receiving the image of an inner surface of a hollow object, such as a flange of an aluminum can, through the opening of the object. This application is based on patent applications No. Hei 8-282688 and No. Hei 9-017146 filed in Japan, the contents of which are incorporated herein by reference.

Figure 7:
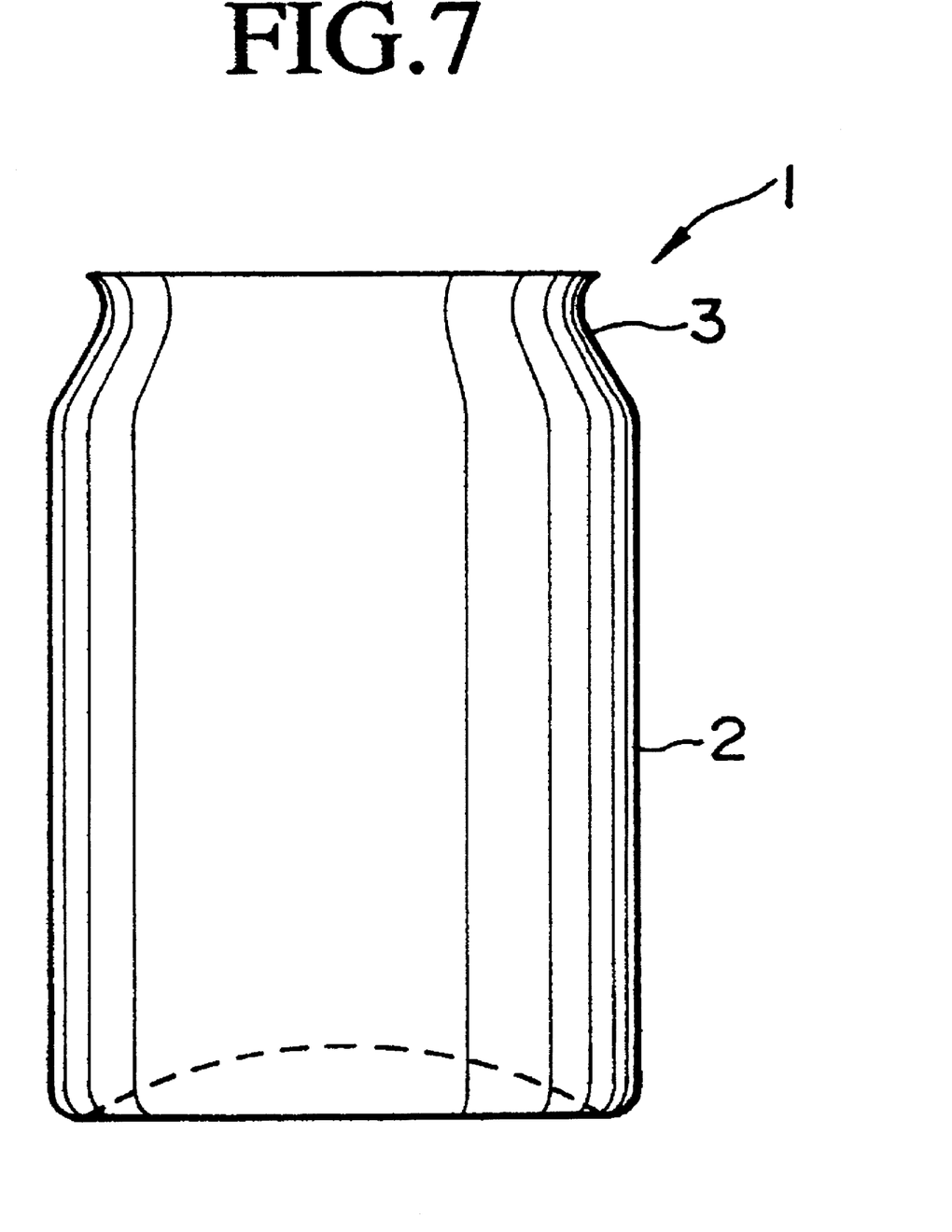
FIG. 7 is a side view of a large aluminum can currently in use.

Large aluminum cans are increasingly being used instead of small cans, because of larger capacity. Although the inner diameter of the middle of the body of the can is large, the top of the body is narrowed. As shown in FIG. 7, the aluminum can 1 comprises a cylindrical body 2 having a closed bottom, and a flange 3 which is narrowed toward the upper opening. Although the flange 3 was formed of a number of steps parallel to the top face, it is recently formed as a curved surface.

When the curved flange 3 is formed in the manufacturing process, defects such as wrinkles (pleats) may occur because the top of the aluminum can is narrowed. An interior image receiving apparatus is used in order to detect the defect on the inner surface of the aluminum can 1. An inner image of the body of the aluminum can 1 can be obtained with a camera of the interior image receiving apparatus using a fisheye lens. However, it is impossible to obtain the image of the inner surface of the narrow flange 3.

In order to obtain the image of the inner surface of the narrow flange 3 in mass production, a camera and an illuminating means are inserted into the aluminum can, and are rotated, receiving an image of the inner surface of the aluminum can 1. Based on the image, an image processing device detects a defect on the inner surface of the aluminum can, which is thereafter removed from the production line. However, because such an interior image receiving operation takes a substantial amount of time, it is impossible to rapidly produce aluminum cans.

SUMMARY OF THE INVENTION

It is an object of the present invention to provide an interior image receiving apparatus and an interior inspecting apparatus with which it is possible to obtain an image of an inner surface of a hollow object in a quick and simple manner.

It is another object of the present invention provide an interior image receiving apparatus and an interior inspecting apparatus with which it is possible to obtain a magnified image of a specified inner surface of a hollow object in order to perform inspection in detail.

In order to accomplish the above object, the interior image receiving apparatus of the present invention comprises:

an image receiver positioned facing an opening of a hollow object; and a reflecting mirror positioned between the image receiver and the opening, wherein the image receiver receives an image of the inner surface of the object reflected by the mirror.

According to the interior image receiving apparatus of the present invention, it is possible to obtain the image of the inner surface of the object through the reflecting mirror in an instant, eliminating rotation of the apparatus or the object and interruption of the transfer of the object.

In the interior image receiving apparatus according to another aspect of the present invention, the mirror is a ring-shaped mirror formed on an inner surface of a support, and the ring-shaped mirror has a center axis coincident with a center axis of the object. According to the apparatus, it is possible to obtain the image of the inner surface of the cylindrical object in an instant.

In the interior image receiving apparatus according to another aspect of the present invention, an inner diameter of the ring-shaped mirror becomes smaller toward the object. According to the apparatus, the mirror is inclined with respect to the optical axis, thereby reflecting the image of a specified portion to the image receiver.

In the interior image receiving apparatus according to another aspect of the present invention, the diameter of the ring-shaped mirror is set to be not less than the maximum inner diameter of the object. According to the apparatus, it is possible to obtain the image of the whole inner surface of the object.

In the interior image receiving apparatus according to another aspect of the present invention, the mirror is formed flat at a section along the axis of the object. According to the apparatus, the undistorted image suitable for optical detection of a defect can be obtained through the flat reflecting mirror.

In the interior image receiving apparatus according to another aspect of the present invention, the mirror is formed concave or convex at a section along the axis of the object. Because the mirror reflects a magnified image of a specified inner surface of the object, it is thereby possible to inspect the specified surface in detail.

In the interior image receiving apparatus according to another aspect of the present invention, the center optical axis of the image receiver corresponds to the center axis of the object. The image obtained by the apparatus includes concentric circles suitable for optical inspection.

In the interior image receiving apparatus according to another aspect of the present invention, the interior image receiving apparatus further comprises an illuminating means for illuminating the inner surface of the object with light. According to the apparatus, because the inside of the object is illuminated, it is possible to obtain a clear image of the inner surface of the object.

In the interior image receiving apparatus according to another aspect of the present invention, the illuminating means has a circular shape which surrounds the image receiver. According to the apparatus, because the inside of the object is evenly illuminated, it is possible to obtain an even clear image of the inner surface.

In the interior image receiving apparatus according to another aspect of the present invention, the interior image receiving apparatus further comprises a hollow cover for enclosing a light path, positioned between the mirror and the image receiver. According to the apparatus, because the illuminating means evenly illuminates the inner surface, it is possible to obtain an even clear image of the inner surface.

In the interior image receiving apparatus according to another aspect of the present invention, the reflecting mirror has a plurality of reflecting faces having different angles with respect to each other. According to the apparatus, because the image of the whole inner surface of the object can be instantly obtained, it is thereby possible to detect a defect such as a fissure on the whole inner surface more easily. The image of the specified portion is obtained through the greater reflecting angle of one of the reflecting faces, so that a defect can be easily detected. The image directly received by the image receiver is distinguished from the image reflected on the reflecting faces, and the image reflected on the one of the reflecting face is distinguished from the image reflected on the other reflecting face. This makes the detection of a defect more reliable.

In another aspect of the present invention, the interior inspecting apparatus for inspecting the inner surface of a hollow object, comprises:

- an image receiver positioned facing an opening of the object;
- a reflecting mirror for reflecting an image of the inner surface of the object to the image receiver and positioned between the image receiver and the opening;
- transfer device for successively transferring a plurality of the objects to be inspected to an inspection position where the image receiver receives the image of the inner surface of the object; and
- determiner for determining the state of the object based on the image of the inner surface of the object.

According to the interior inspecting apparatus of the present invention, because it is possible to obtain the image of the inner surface of the object in an instant, eliminating rotation of the apparatus or the object and interruption of the transfer of the object, the inspection of the object can be quickly completed.

In the interior inspecting apparatus according to another aspect of the present invention, the apparatus further comprises an illuminating means for illuminating the inner surface of the object with light. According to the apparatus, because a clear image of the inner surface of the object is obtained, it is thereby possible to inspect the inner surface in detail.

DETAILED DESCRIPTION OF THE PREFERRED EMBODIMENTS

First Embodiment

Referring to FIGS. 1 to 4, the best mode of the interior image receiving apparatus according to the first embodiment of the present invention, will be explained.

Figure 1:
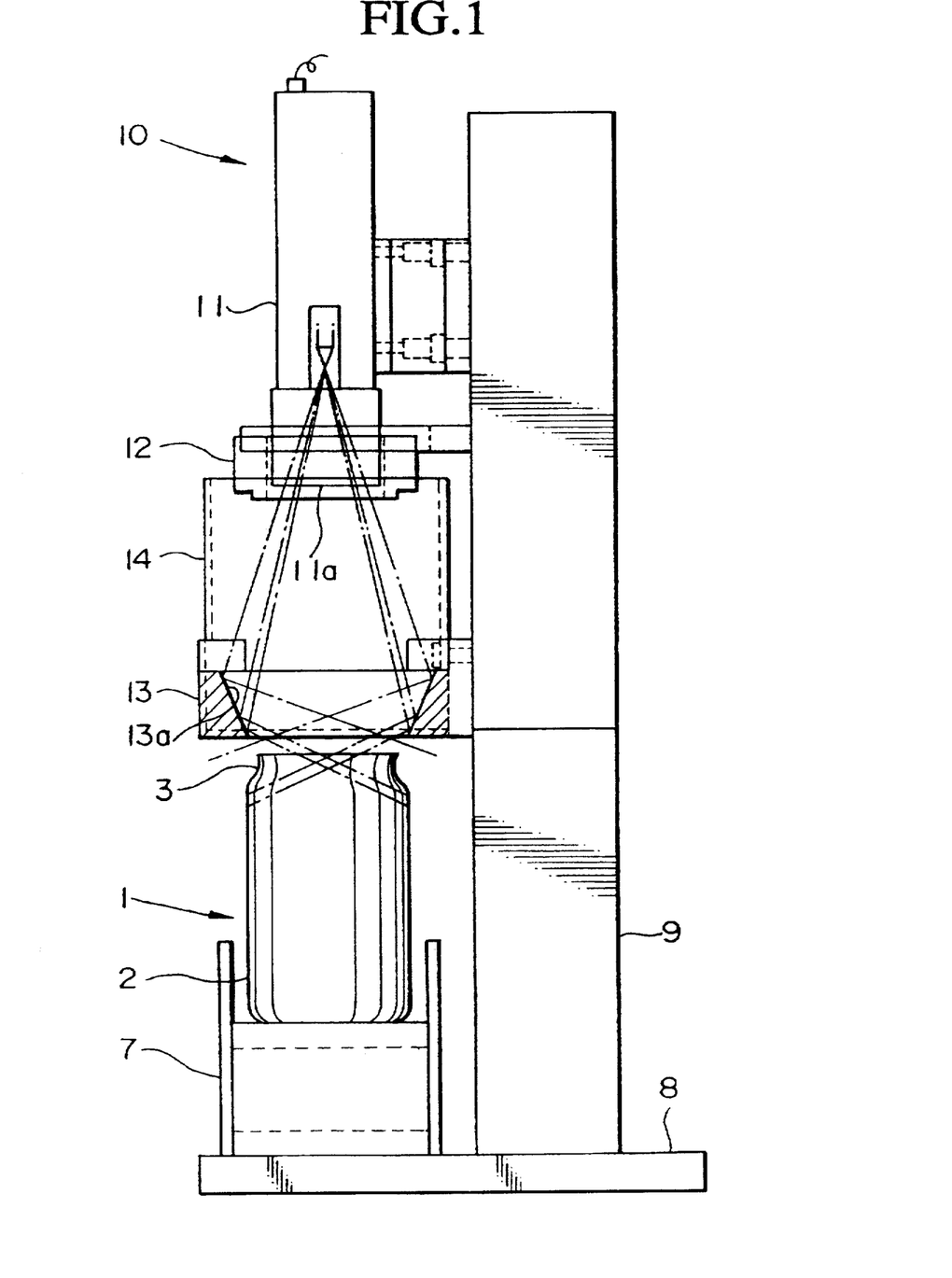
FIG. 1 is a side view of a first embodiment of an interior image receiving apparatus of the present invention.

As shown in FIG. 1, the interior inspecting apparatus comprises a base 8, a belt conveyer 7, which is a transfer device for successively transferring aluminum cans 1, a vertical post 9 fixed at the edge of the base 8, and the interior image receiving apparatus 10 attached to the post 9.

In the interior image receiving apparatus 10, a camera 11 which is an image receiver is attached to the upper portion of the post 9, facing the top of the aluminum can 1. The camera 11 has a wide-angle lens 11a, around which a ring-shaped illuminating means 12, for example, a stroboscope or a light flash means, is mounted. An inspection position for the aluminum can 1 is predetermined on the belt conveyer 7 directly under the camera 11. The center axis of the camera 11 corresponds to the center axis of the aluminum can 1 which is positioned at the inspection position.

Figure 2:
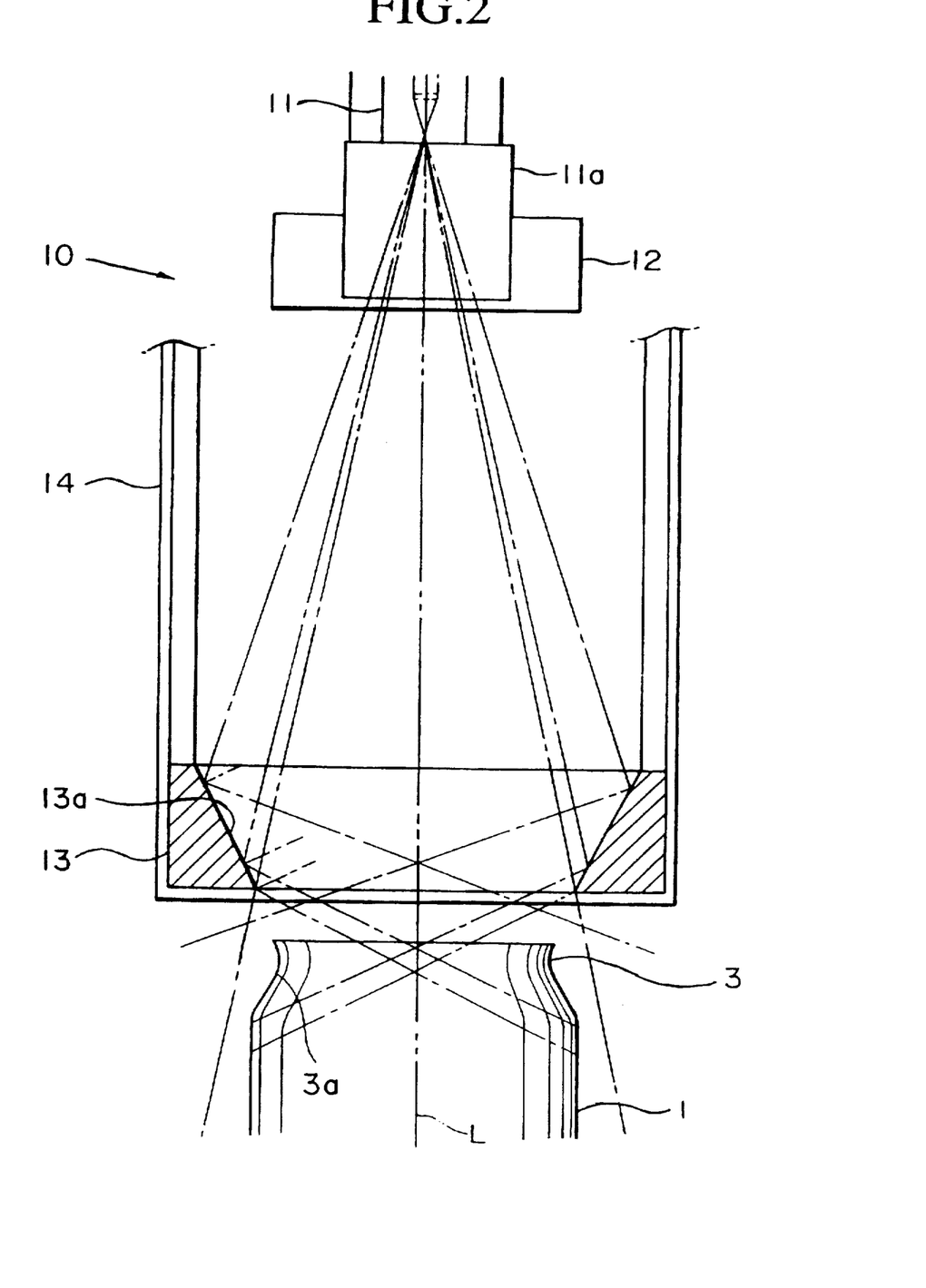
FIG. 2 is side view of a reflecting mirror and light path of the first embodiment.
Figure 3:
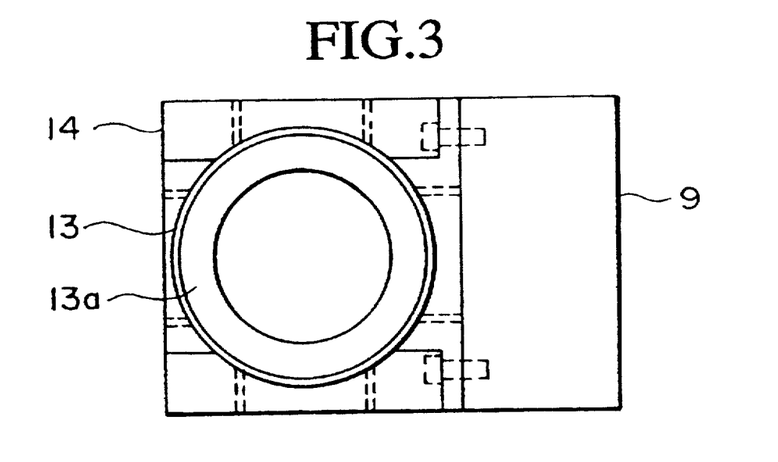
FIG. 3 is a top view of the reflecting mirror of the first embodiment.

A reflecting mirror support 13 is attached to the post 9, slightly apart from the flange 3 of the top opening of the aluminum can 1 at the inspection position. As shown in FIG. 2, a round hole is vertically made in the reflecting mirror support 13, and a ring-shaped reflecting mirror 13a is formed on the inner surface of the hole of the reflecting mirror support 13 (also as shown in FIG. 3). The inner diameter of the reflecting mirror 13a becomes smaller toward the aluminum can 1. In other words, the reflecting mirror 13a is tapered to form a conical inner surface.

The reflecting mirror 13a is formed flat at a section along the center axis of the aluminum can 1. The inner diameter of the reflecting mirror 13a near the aluminum can 1 is set to be not less than the inner diameter of the flange 3 of the aluminum can 1. The reflecting mirror 13a has a center axis coincident with a center axis L of the aluminum can 1.

The angle of the reflecting mirror 13a is adjusted so that an image of the whole inner surface 3a of the flange 3 is reflected on the reflecting mirror 13a toward the camera 11. Further, the height of the reflecting mirror 13a is determined so that the inspection can be performed irrespective of a certain amount of aberration from the inspection position or from the shot timing.

A hollow cover 14 is positioned between the lens 11a of the camera 11 and the reflecting mirror support 13 in order to enclose the light path, so that the illuminating means 12 evenly illuminates the inner surface 3a of the flange 3. Further, because the light from the illuminating means 12 is reflected on the bottom of the aluminum can 1, the whole inner surface 3a of the flange 3 is evenly illuminated.

Next, the operation of the interior image receiving apparatus 10 will be explained with reference to FIG. 1. The aluminum can 1 is being successively transferred with the belt conveyer 7 to the inspection position, where the center optical axis of the camera 11 corresponds to the center axis of the aluminum can 1. When a sensor (not shown) detects that the aluminum can 1 is positioned at the inspection position, the illuminating means 12 illuminates the inside of the aluminum can 1 through the top opening in exact timing. Synchronized with the momentary illumination, the camera 11 receives the image of the inner surface 3a of the flange 3 of the aluminum can 1 which is reflected on the reflecting mirror 13a, at which moment the static composite image of the inner surface 3a is obtained.

Figure 4:
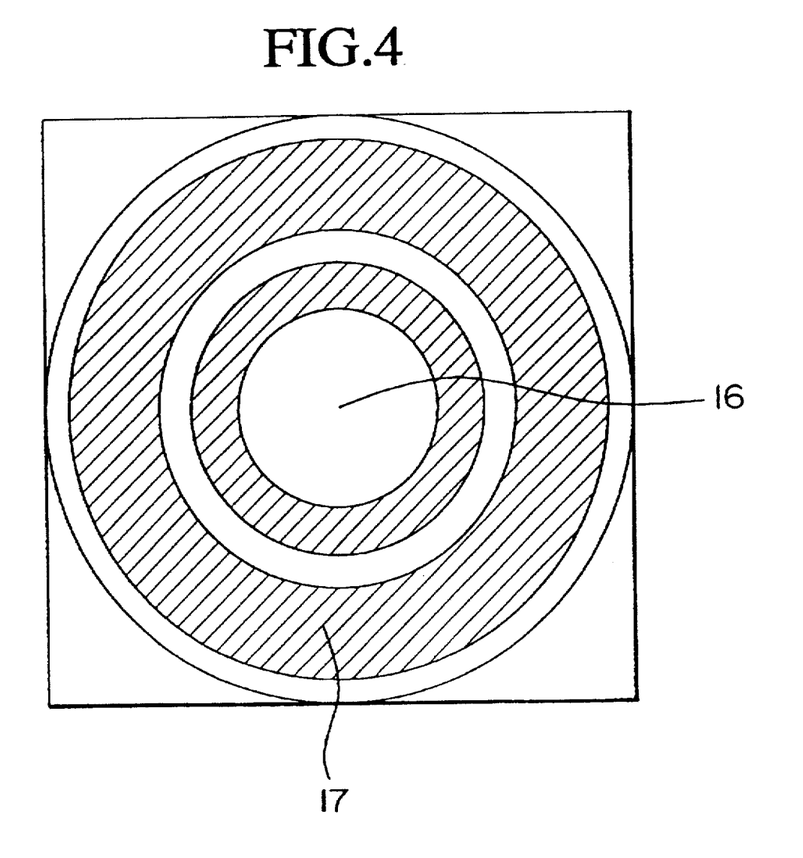
FIG. 4 shows an image obtained through the reflecting mirror of the first embodiment.

FIG. 4 shows an example of the composite image of the inside of the aluminum can 1 obtained through the above-explained operation. A center round portion 16 indicates the bottom of the aluminum can 1, and circumferences 17 indicate the inner surface 3a of the flange 3. Namely, the composite image includes the image of the inner surface 3a reflected on the reflecting mirror 13 and the image of the bottom and the periphery directly received by the camera 11.

The image is provided to a determiner (not shown), which determines whether or not the aluminum can 1 has a defect. When the defect is found by the determiner, the aluminum can 1 is removed from the production line.

According to the interior image receiving apparatus 10, it is possible to obtain the image of the inner surface 3a through the reflecting mirror 13a in an instant, eliminating rotation of the apparatus 10 or the aluminum can 1 and interruption of the transfer of the aluminum can 1. Accordingly, the inspection of the aluminum can 1 can be quickly completed.

Because the reflecting mirror 13a is a ring-shaped mirror formed on an inner surface of a support 13 and has the center axis coincident with the center axis of the aluminum can 1, it is thereby possible to obtain the image of the inner surface 3a of the cylindrical can 1 in an instant.

The inner diameter of the reflecting mirror 13a becomes smaller toward the top of the aluminum can 1, so that the reflecting mirror 13a is inclined with respect to the optical axis, thereby reflecting the image of the inner surface 3a to the camera 11.

Because the diameter of the reflecting mirror 13 is set to be not less than the inner diameter of the aluminum can 1, it is possible to obtain the image of the whole inner surface 3a of the aluminum can 1.

The reflecting mirror 13a is formed flat at a section along the center axis of the aluminum can 1, so that the undistorted image suitable for optical inspection of a defect can be obtained through the flat reflecting mirror 13a.

Because the center optical axis of the camera 11 corresponds to the center axis of the aluminum can 1, the image obtained by the apparatus 10 includes the concentric circles suitable for optical inspection.

Additionally, because the interior image receiving apparatus is installed in the established inspection line, the inspection line can be improved at low cost.

Figure 5:
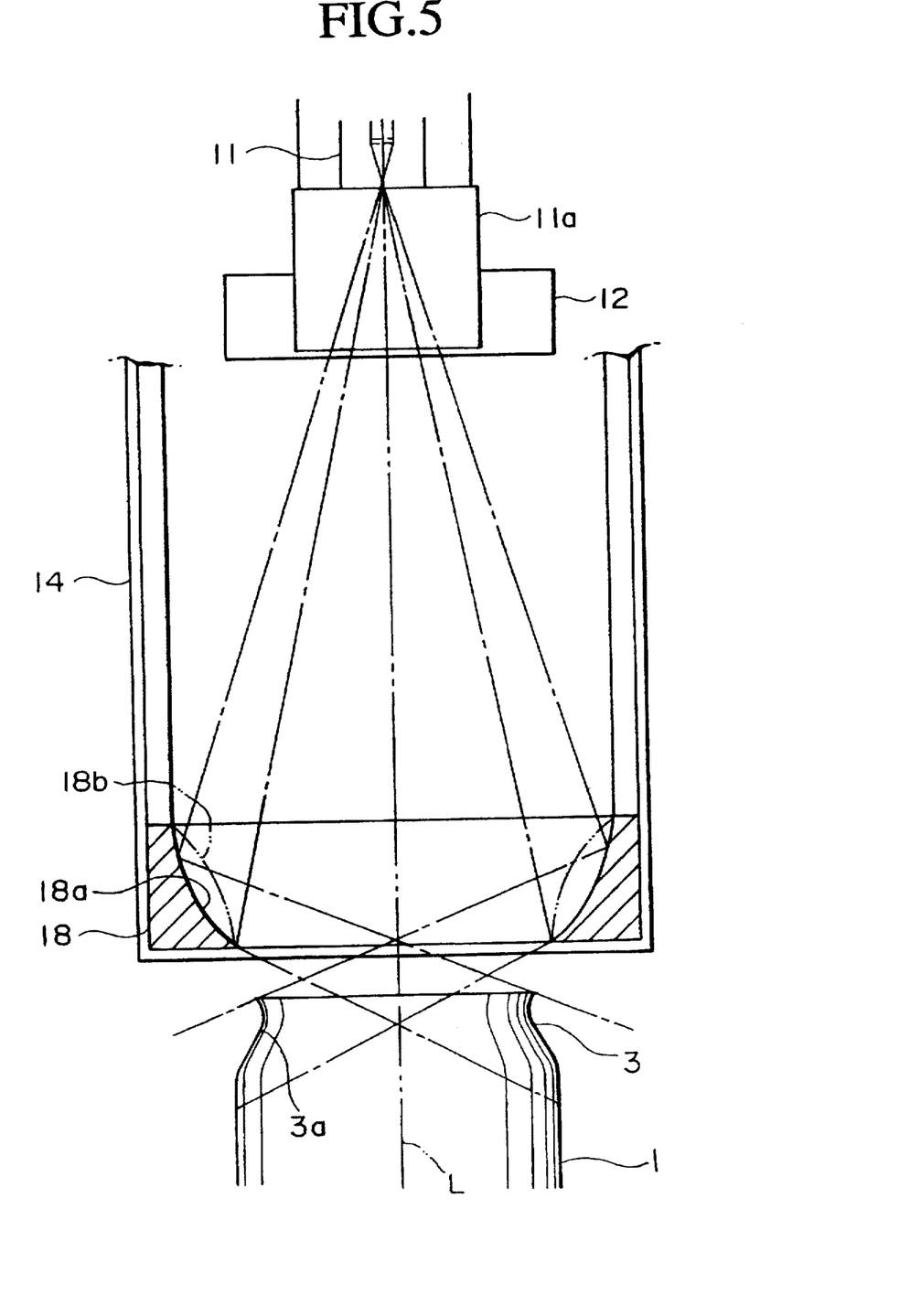
FIG. 5 shows a modified example of the reflecting mirror of the first embodiment.

FIG. 5 shows a modified example of the first embodiment. In the interior image receiving apparatus 10, the reflecting mirror 18a is formed concave at a section along the center axis L of the aluminum can 1. The inner diameter of the reflecting mirror 18a formed in the reflecting mirror support 18 becomes smaller toward the aluminum can 1.

Besides, the reflecting mirror 18b may be formed convex at a section along the center axis L of the aluminum can 1, as defined by the double dashed line. The inner diameter of the reflecting mirror 18a formed in the reflecting mirror support 18 becomes smaller toward the aluminum can 1.

Because the reflecting mirrors 18a or 18b are formed concave or convex at a section along the axis L of the aluminum can 1, the reflecting mirrors 18a or 18b provide the magnified image of the inner surface of the flange 3a, and it is thereby possible to inspect the inner surface 3a in detail.

Second Embodiment

Figure 6:
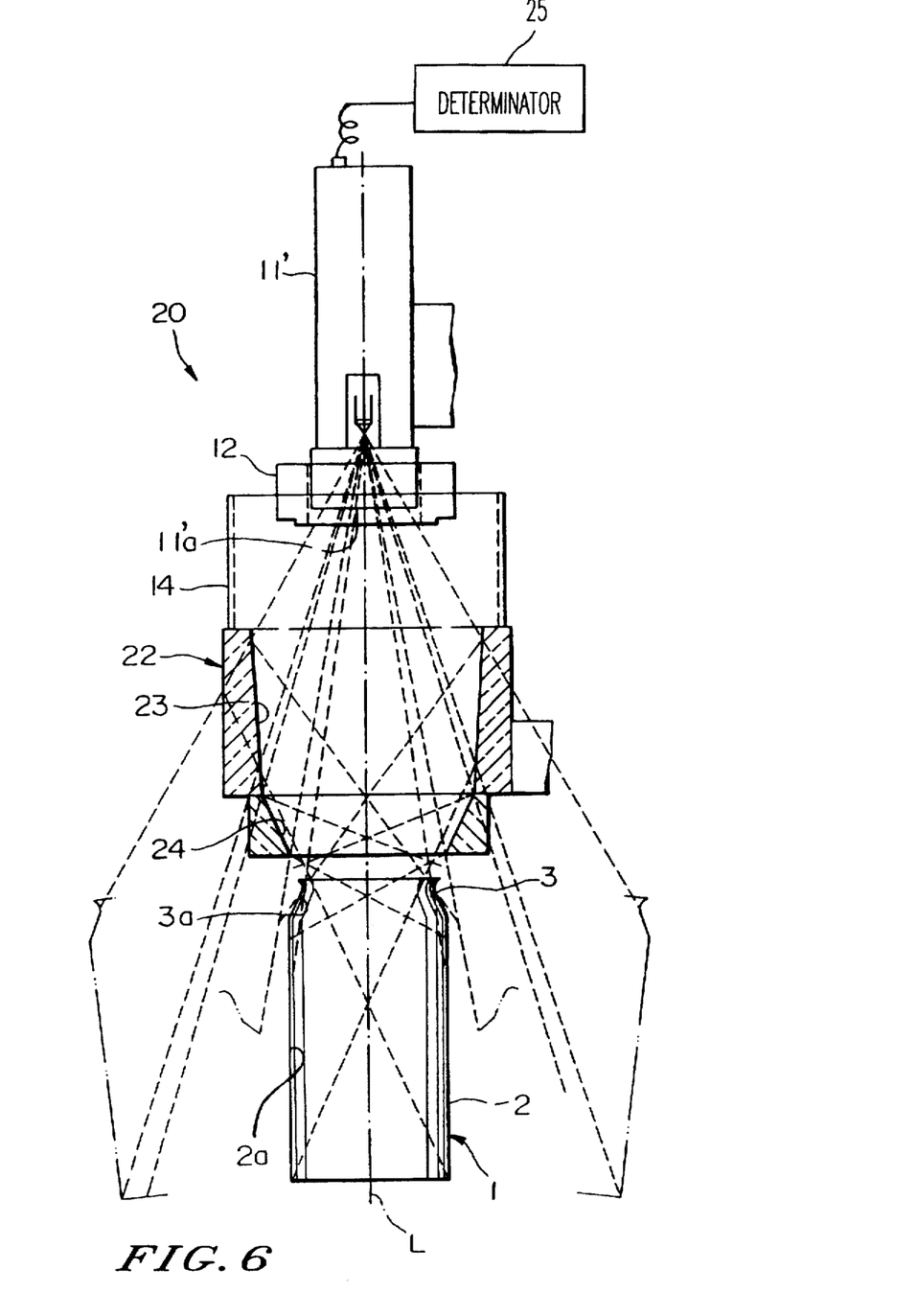
FIG. 6 is a side view of a second embodiment of an interior image receiving apparatus of the present invention.

Next, referring to FIG. 6, the second embodiment of the present invention will be explained. In FIG. 6, reference numerals which are identical to those of FIGS. 1 to 5, respectively, indicate elements which are identical to those of the first embodiment; therefore, explanation thereof will be omitted.

A interior image receiving apparatus 20 of the second embodiment is fixed to the vertical post (not shown) in a similar manner of the first embodiment. A reflecting mirror support 22 is positioned between the camera 11' and the aluminum can 1 placed at the inspection position. A hollow cover 14 is positioned between the camera 11' and the reflecting mirror support 22 in order to enclose the light path. The camera 11' is an area camera with wide-angle lens 11a which can be focused on the whole inner surface of the aluminum can 1.

A round hole is made in the reflecting mirror support 22, and ring-shaped reflecting faces (mirrors) 23 and 24 are formed on the inner surface of the hole. The reflecting faces 23 and 24 have different angles from each other. The angle of the first reflecting face 23 near the camera 11' is small with respect to the center axis L, so that the first reflecting face 23 reflects the image of the whole inner surface 2a of the aluminum can 1 toward the camera 11'.

The angle of the second reflecting face 24 combined under the first reflecting face 23 is greater than the angle of the first reflecting face 23 with respect to the center axis L, so that the second reflecting face 24 reflects the magnified image of the inner surface 2a of the flange 3 toward the camera 11'.

The center axis of the first reflecting face 23 corresponds to that of the second reflecting face 24. The inner diameters of the reflecting faces 23 and 24 become smaller toward the aluminum can 1. The diameter of the second reflecting face 24 is set to be not less than that of the first reflecting face 23 at the joint of the first and second reflecting faces 23 and 24.

Next, the operation of the interior image receiving apparatus 20 will be explained. An aluminum can 1 is being successively transferred on the belt conveyer 7 (shown in FIG. 1) to the inspection position, where the center optical axis of the camera 11' corresponds to the center axis of the aluminum can 1. When a sensor (not shown) detects that the aluminum can 1 is positioned at the inspection position, the illuminating means 12 illuminates the inside of the aluminum can 1 through the top opening in exact timing. Synchronized with the momentary illumination, the camera 11' receives the image of the inner surface 3a of the flange 3 of the aluminum can 1 which is reflected on the reflecting faces 23 and 24, at which moment the static composite imaged of the inner surfaces 2a and 3a are obtained.

The image obtained by the interior image receiving apparatus 20 includes the image of the bottom of the aluminum can 1 directly received by the camera 11', the image of the flange 3 which is reflected on the second reflecting face 24 and positioned as to surround the image of the bottom, and the image of the inner side 2a of the body 2 which is reflected on the first reflecting face 23 and positioned as to surround the image of the flange 3. Namely, these three images form concentric circles. When the inner diameter of the second reflecting face 24 is set greater, an image which partly includes the inner vertical surface may be obtained.

The image is provided to a determinator 25, which determines whether or not the aluminum can 1 has a defect. When the defect is found by the determinater, the aluminum can 1 is removed from the production line.

Because the image of the whole inner surface of the aluminum can 1 can be instantly obtained with the interior image receiving apparatus 20 of the second embodiment, it is thereby possible to detect a defect such as a fissure on the whole inner surface more easily than the first embodiment. The image of the flange 3 is obtained with the reflecting face 24 having the greater reflecting angle, so that a defect can be easily detected. The image directly received by the camera 11' is distinguished from the images reflected on the reflecting faces 23 and 24, and the image obtained through the greater reflecting angle is distinguished from the image obtained through the less reflecting angle. This makes the detection of a defect more reliable.

Although the second embodiment comprises two reflecting faces 23 and 24, it may comprise three or more reflecting mirrors. In this case, the diameter of the reflecting mirror near the aluminum can 1 is preferably set to be not less than that of the other reflecting mirror at the joint of the adjacent reflecting mirrors. When a surface other than the flange 3 is inspected, the angle of the reflecting face 23 may be changed.

The image of the whole inner surface 2a is not always needed. The inspection can also be performed based on the partial image of the inner surface of the aluminum can 1. The two reflecting faces 23 and 24 may be integrally molded or may be formed concave or convex at a section along the center axis of the aluminum can 1. Additionally, reflecting mirrors, having different sectional shapes from each other, may be combined together.

Although the interior image receiving apparatuses 10 and 20 receive the image of the narrow inner surface 3a of the flange 3, it is also possible to receive an image of an inner surface of a can which has no narrowed flange. Further, the image receiving operation may be performed when the aluminum can is not only being moved but when it is stopped. The illuminating means 12 which is employed in the embodiments is not always necessary. The invention can also be applied to a hollow object other than the aluminum can 1.

What is claimed is:

1. An interior image receiving apparatus, comprising:
   an image receiver positioned facing an opening of a hollow object; and
   a reflecting mirror positioned between said image receiver and said opening,
   wherein said image receiver receives an image of the inner surface of said object reflected by said mirror,
   wherein said mirror is a ring-shaped mirror formed on an inner surface of a support, and said ring-shaped mirror has a center axis coincident with a center axis of said object,
   wherein said mirror includes a first portion having a first inclined reflecting surface and at least a second portion having at least a second inclined reflecting surface positioned at a section along said axis of said object, and
   wherein said first inclined reflecting surface comprises a different angle of inclination than said second inclined reflecting surface.

2. The interior image receiving apparatus according to claim 1, wherein an inner diameter of said ring-shaped mirror becomes smaller toward said object.

3. The interior image receiving apparatus according to claim 1, wherein the diameter of said ring-shaped mirror is set to be not less than the maximum inner diameter of said object.

4. The interior image receiving apparatus according to claim 1, wherein said mirror is formed concave or convex at a section along said axis of said object.

5. The interior image receiving apparatus according to claim 1, wherein the center optical axis of said image receiver corresponds to said center axis of said object.

6. The interior image receiving apparatus according to claim 1, further comprising an illuminating means for illuminating the inner surface of said object with light.

7. The interior image receiving apparatus according to claim 6, wherein said illuminating means has a circular shape which surrounds said image receiver.

8. The interior image receiving apparatus according to claim 6, further comprising a hollow cover for enclosing a light path, positioned between said mirror and said image receiver.

9. An interior inspecting apparatus for inspecting the inner surface of a hollow object, comprising:
   an image receiver positioned facing an opening of said object;
   a reflecting mirror for reflecting an image of the inner surface of said object to said image receiver and positioned between said image receiver and said opening;
   transfer device for successively transferring a plurality of objects to an inspection position where said image receiver receives the image of the inner surface of said object; and
   a determinator for determining the state of said object based on the image of the inner surface of said object,
   wherein said mirror is a ring-shaped mirror formed on an inner surface of a support, and said ring-shaped mirror has a center axis coincident with a center axis of said object,
   wherein said mirror includes a first portion having a first inclined reflecting surface and at least a second portion having at least a second inclined reflecting surface positioned at a section along said axis of said object, and
   wherein said first inclined reflecting surface comprises a different angle of inclination than said second inclined reflecting surface.

10. The interior inspecting apparatus according to claim 9, further comprising an illuminating means for illuminating the inner surface of said object with light.

11. An interior image receiving apparatus, comprising:
    an image receiver position facing an opening of a hollow object;
    a first reflecting mirror having a first inclined reflecting surface positioned at a section along an axis of said object and between said image receiver and said opening; and
    at least a second reflecting mirror having at least a second inclined reflecting surface positioned between said first reflecting mirror and said opening,
    wherein said image receiver receives a first image of an inner surface of a body of said object reflected by said first mirror and a second image of an inner surface of a flange of said object reflected by said at least said second mirror, and
    wherein said first inclined reflecting surface comprises a different angle of inclination than said second inclined reflecting surface.

12. The interior image receiving apparatus according to claim 11, wherein said first mirror and said at least said second mirror are ring-shaped mirrors formed on an inner surface of a support, and having a center axis coincident with a center axis of said object.

13. The interior image receiving apparatus according to claim 12, wherein an inner diameter of said ring-shaped mirrors becomes smaller toward said object.

14. The interior image receiving apparatus according to claim 12, wherein the diameter of said ring-shaped mirrors is set to be not less than the maximum inner diameter of said object.

15. The interior image receiving apparatus according to claim 12, wherein the center optical axis of said image receiver corresponds to said center axis of said object.

16. The interior image receiving apparatus according to claim 11, wherein said at least said second mirror is formed concave or convex at a section along said axis of said object.

17. The interior image receiving apparatus according to claim 11, further comprising:
    an illuminating means for illuminating the inner surface of said object with light.

18. The interior image receiving apparatus according to claim 17, wherein said illuminating means has a circular shape which surrounds said image receiver.

19. The interior image receiving apparatus according to claim 17, further comprising:
    a hollow cover for enclosing a light path, positioned between said first mirror and said image receiver.

* * * * *